(12) United States Patent
Taniguchi et al.

(10) Patent No.: US 11,154,220 B2
(45) Date of Patent: Oct. 26, 2021

(54) INFORMATION PROCESSING APPARATUS, METHOD, AND INFORMATION PROCESSING SYSTEM FOR INFERRING A MOVEMENT DESTINATION OF A PERSON BY UTILIZING A WIRELESS DEVICE

(71) Applicants: Ryu Taniguchi, Kanagawa (JP); Masanori Nakagawa, Kanagawa (JP)

(72) Inventors: Ryu Taniguchi, Kanagawa (JP); Masanori Nakagawa, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 16/890,257

(22) Filed: Jun. 2, 2020

(65) Prior Publication Data

US 2020/0375504 A1 Dec. 3, 2020

(30) Foreign Application Priority Data

Jun. 3, 2019 (JP) .............................. JP2019-103981
May 8, 2020 (JP) .............................. JP2020-082848

(51) Int. Cl.
*A61B 5/11* (2006.01)
*A61B 5/00* (2006.01)
*H04W 4/029* (2018.01)
*G06N 20/00* (2019.01)

(52) U.S. Cl.
CPC .......... *A61B 5/1113* (2013.01); *A61B 5/0022* (2013.01); *A61B 5/0024* (2013.01); *G06N 20/00* (2019.01); *H04W 4/029* (2018.02)

(58) Field of Classification Search
CPC ... A61B 5/1113; A61B 5/0022; A61B 5/0024; H04W 4/029; G06N 20/00
See application file for complete search history.

(56) References Cited

U.S. PATENT DOCUMENTS

| | | | |
|---|---|---|---|
| 2011/0125514 A1* | 5/2011 | Molaison ............... | G16H 40/63 705/2 |
| 2016/0029966 A1* | 2/2016 | Salas-Boni ........ | A61B 5/14532 600/347 |
| 2016/0187139 A1* | 6/2016 | Agulnik ................. | G06Q 50/26 701/409 |
| 2017/0061090 A1 | 3/2017 | Itoh | |
| 2017/0153115 A1* | 6/2017 | Vandanapu ........ | G01C 21/3605 |

FOREIGN PATENT DOCUMENTS

JP 2017-049831 3/2017

* cited by examiner

*Primary Examiner* — Hongmin Fan
(74) *Attorney, Agent, or Firm* — IPUSA, PLLC

(57) ABSTRACT

An information processing apparatus includes a processor, in communication with a memory, executing a process including acquiring identification information of a wireless device and information for identifying a position of the wireless device; storing a learned model generated by performing machine learning by using a training dataset including a position of a person to which the wireless device is attached and a movement destination of the person to which the wireless device is attached; inferring the movement destination of the person to which the wireless device is attached from the position of the wireless device, based on the learned model; and reporting the inferred movement destination.

8 Claims, 15 Drawing Sheets

FIG.4A

PRE-CONVERSION DATA

| date time | tagID | ANTENNA ID |
|---|---|---|
| 2019/11/1 12:01 | 0X345R | antn001 |
| 2019/11/1 12:01 | 0X234W | antn015 |
| ⋮ | ⋮ | ⋮ |
| 2019/11/1 12:01 | 0X211Q | antn044 |

FIG.4B

POST-CONVERSION DATA

| date time | person | 101 | 102 | ... | 505 |
|---|---|---|---|---|---|
| 2019/11/1 12:01 | nurse A | 0 | 1 | ... | 0 |
| 2019/11/1 12:01 | nurse B | 1 | 0 | ... | 0 |
| ⋮ | ⋮ | ⋮ | ⋮ | ⋮ | ⋮ |
| 2019/11/1 12:01 | nurse C | 0 | 0 | ... | 1 |

FIG.5

| date time | person | 101,102, ···,505 |
|---|---|---|
| 2019/11/1 12:00 | nurse A | [0,1,···,0] |
| 2019/11/1 12:05 | nurse A | [1,0,···,0] |
| 2019/11/1 12:10 | nurse A | [0,0,···,1] |
| 2019/11/1 12:15 | nurse A | [0,1,···,0] |
| 2019/11/1 12:20 | nurse A | [0,1,···,0] |

FIG.14

| PARAMETER | VALUE |
|---|---|
| NUMBER OF STEPS | 3,5,10 |
| MINI BATCH SIZE | 128 |
| NUMBER OF TIMES OF LEARNING | 25 |

FIG.15A

TABLE: INPUT

| date_time | 101,102,···,505 |
|---|---|
| 2019/11/1 12:10 | [0,1,···,0] |
| 2019/11/1 12:15 | [1,0,···,0] |
| 2019/11/1 12:20 | [0,1, ··,0] |

FIG.15B

TABLE: OUTPUT

| date_time | 101,102,···,505 |
|---|---|
| 2019/11/1 12:25 | [0.85,0.10,···,0.01] |

FIG.16A

TABLE: INPUT

| date_time | person | 101,102,⋯,505 |
|---|---|---|
| 2019/11/1 12:10 | nurse A | [0,1,⋯,0] |
| 2019/11/1 12:15 | nurse A | [1,0,⋯,0] |
| 2019/11/1 12:20 | nurse A | [0,1,⋯,0] |

FIG.16B

TABLE: OUTPUT

| date_time | person | 101,102,⋯,505 | action |
|---|---|---|---|
| 2019/11/1 12:25 | nurse A | [0.85,0.10,⋯,0.01] | medical_examination |

INFORMATION PROCESSING APPARATUS, METHOD, AND INFORMATION PROCESSING SYSTEM FOR INFERRING A MOVEMENT DESTINATION OF A PERSON BY UTILIZING A WIRELESS DEVICE

CROSS-REFERENCE TO RELATED APPLICATION

The present application is based on and claims priority under 35 U.S.C. § 119 to Japanese Patent Application No. 2019-103981, filed on Jun. 3, 2019, and Japanese Patent Application No. 2020-082848, filed on May 8, 2020, the contents of which are incorporated herein by reference in their entirety.

BACKGROUND OF THE INVENTION

1. Field of the Invention

The present invention relates to an information processing apparatus, a method, and an information processing system.

2. Description of the Related Art

In the related art, there is a known technique for managing position information of medical staff such as nurses (also referred to as "healthcare professionals") within a medical facility such as a hospital. For example, Patent Document 1 discloses a technique for centrally managing position information of persona involved in medical care (e.g., a patient, a physician, a nurse, etc.) and the medical information of a patient.

Patent Document 1: Japanese Unexamined Patent Application Publication No. 2017-049831

SUMMARY OF THE INVENTION

According to one aspect of the present invention, there is provided an information processing apparatus including a processor, in communication with a memory, executing a process including acquiring identification information of a wireless device and information for identifying a position of the wireless device; storing a learned model generated by performing machine learning by using a training dataset including a position of a person to which the wireless device is attached and a movement destination of the person to which the wireless device is attached; inferring the movement destination of the person to which the wireless device is attached from the position of the wireless device, based on the learned model; and reporting the inferred movement destination.

BRIEF DESCRIPTION OF THE DRAWINGS

FIGS. 4A and 4B are diagrams for explaining pre-conversion data and post-conversion data according to an embodiment of the present invention;

FIG. 5 illustrates an example of data stored in a training dataset storage unit according to an embodiment of the present invention;

FIG. 14 illustrates operational parameters in an LSTM model according to an embodiment of the present invention;

FIGS. 15A and 15B illustrate data formats of input data and output data according to an embodiment of the present invention; and FIGS. 16A and 16B illustrate data formats of input data and output data according to an embodiment of the present invention.

DETAILED DESCRIPTION OF THE PREFERRED EMBODIMENTS

Figure 1:
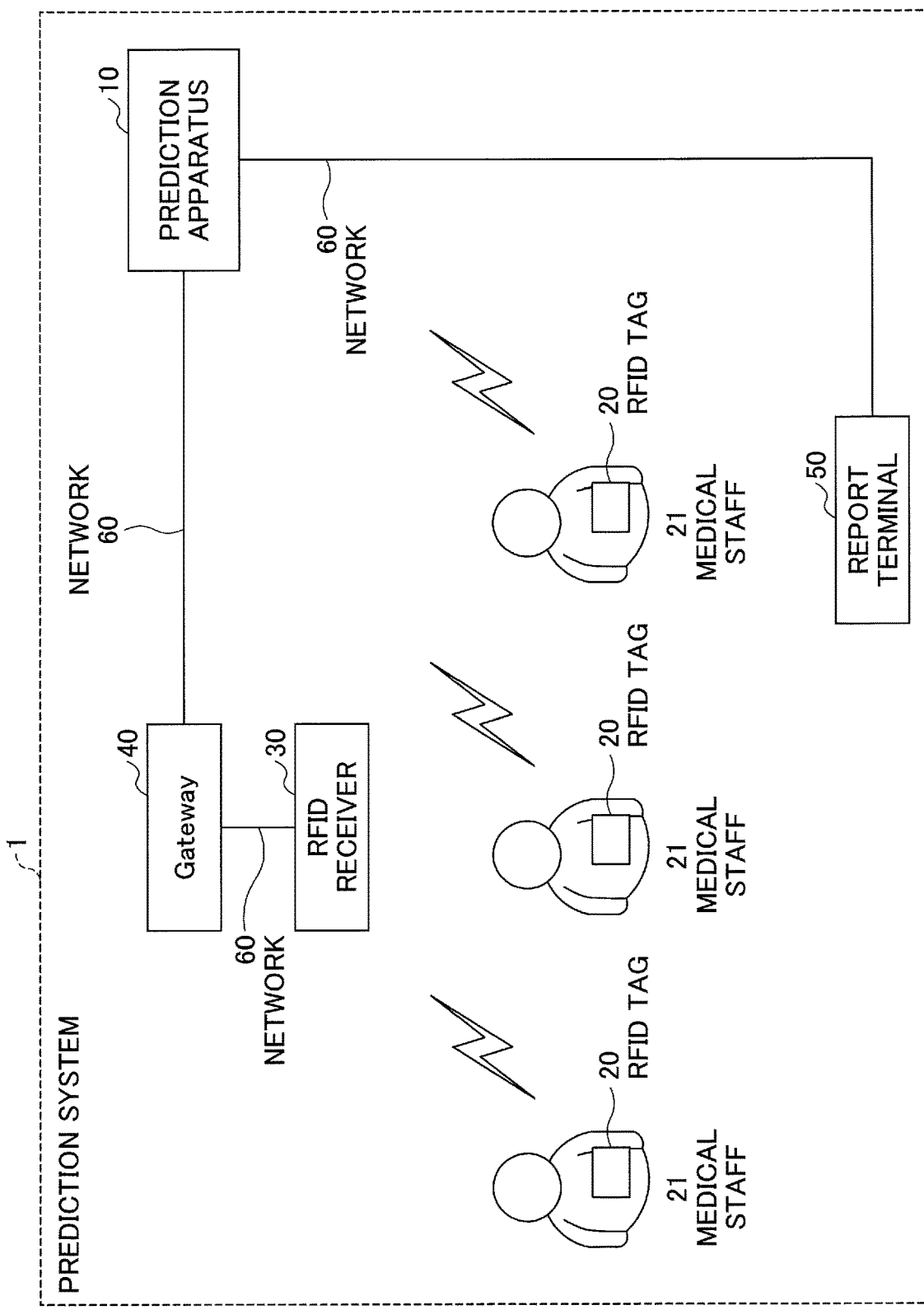
FIG. 1 is a configuration diagram of the entire prediction system according to an embodiment of the present invention.

In medical facilities such as hospitals, etc., medical staff need to know which patient room to go to next after completing work at the present position, in order to efficiently move among patient rooms, etc. However, in Patent Document 1, although the patient's medical information and the present position of the medical staff member and the like can be centrally managed, it has not been possible to present the destination of movement (movement destination) of the medical staff member and the like.

A problem to be addressed by an embodiment of the present invention is to predict the movement destination of a person, such as a medical staff member, to which a wireless device is attached (a person wearing or carrying a wireless device).

Hereinafter, each embodiment will be described with reference to the accompanying drawings. In the present specification and the drawings, for the elements having substantially the same functional configuration, overlapping descriptions are omitted by denoting the same elements by the same reference numerals.

<System Configuration>

FIG. 1 is a diagram of the entire configuration of a prediction system 1 (an example of an information processing system) according to an embodiment of the present invention. As illustrated in FIG. 1, the prediction system 1 includes a prediction apparatus 10 (an example of an information processing apparatus), a radio frequency identifier (RFID) tag 20, an RFID receiver 30, a Gateway 40, and a report terminal 50. The prediction apparatus 10 may receive data from the RFID receiver 30 via the Gateway 40 via any network 60. The prediction apparatus 10 can transmit data to the report terminal 50 via any network 60. Each of these elements will be described below.

It is assumed that the RFID tag 20 is attached to a medical staff member 21 (that the medical staff member 21 is wearing or carrying the RFID tag 20).

Figure 3:
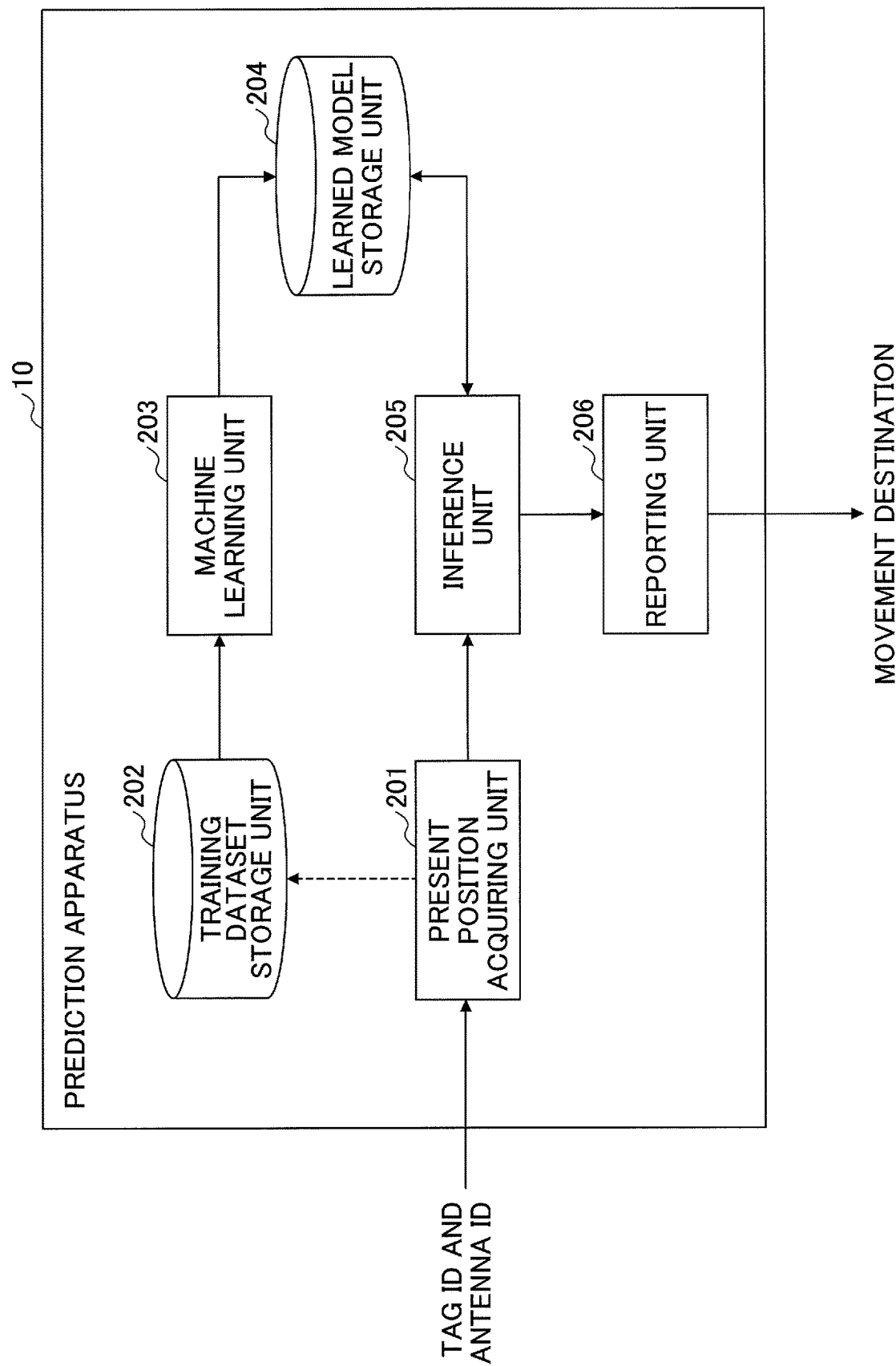
FIG. 3 is a functional block diagram of the prediction apparatus according to an embodiment of the present invention.

The prediction apparatus 10 acquires the present position of the medical staff member 21 and predicts the position of the next movement destination (i.e., the next position) to which the medical staff member 21 is to go. The prediction apparatus 10 can report, to the report terminal 50, the information of the position of the movement destination (the location of the destination). With reference to FIG. 3, the prediction apparatus 10 will be described in detail later.

The RFID tag 20, the RFID receiver 30, and the Gateway 40 perform processes to acquire the present position of the medical staff member 21.

The RFID tag 20 is embedded with identification information (hereinafter referred to as a tag ID) for identifying the RFID tag 20. As noted above, the RFID tag 20 is attached to the medical staff member 21.

The RFID receiver 30 is provided with identification information (hereinafter, referred to as an antenna ID) for identifying the RFID receiver 30. For example, the RFID receiver 30 is located on the ceiling or the like of each patient room or the like in the hospital. The RFID receiver 30 receives the tag ID from the RFID tag 20 via Near Field Communication. The RFID receiver 30 also transmits the tag ID and antenna ID to the Gateway 40.

The Gateway 40 transmits collected data from the RFID receiver 30 to the prediction apparatus 10. For example, the Gateway 40 receives tag IDs and antenna IDs from the RFID receivers 30 installed in a plurality of patient rooms or the like and transmits the tag IDs and antenna IDs to the prediction apparatus 10.

The method for acquiring the present position of the medical staff member 21 is not limited to the method using the RFID as described above, but may be any method such as the method using a beacon. That is, any relevant method may be used as long as it is possible to acquire information (e.g., an antenna ID) for identifying the position of any wireless device (e.g., the RFID tag 20) attached to the medical staff member 21.

The report terminal 50 acquires the information of the position of the movement destination of the medical staff member 21, from the prediction apparatus 10, and presents the information to the medical staff member 21 or the like. For example, the report terminal 50 may be a digital signage, a smartphone, a tablet, a personal computer, a wearable device worn by the medical staff member 21, or the like, installed within the hospital. The report terminal 50 may display the information of the position of the movement destination on the screen or may output the information of the position of the movement destination by voice sound.

Note that the group of devices described in the embodiment are merely indicative of one of a plurality of computing environments for carrying out the embodiments described herein. For example, the prediction apparatus 10 may be implemented by a plurality of computers.

<Hardware Configuration>

Figure 2:
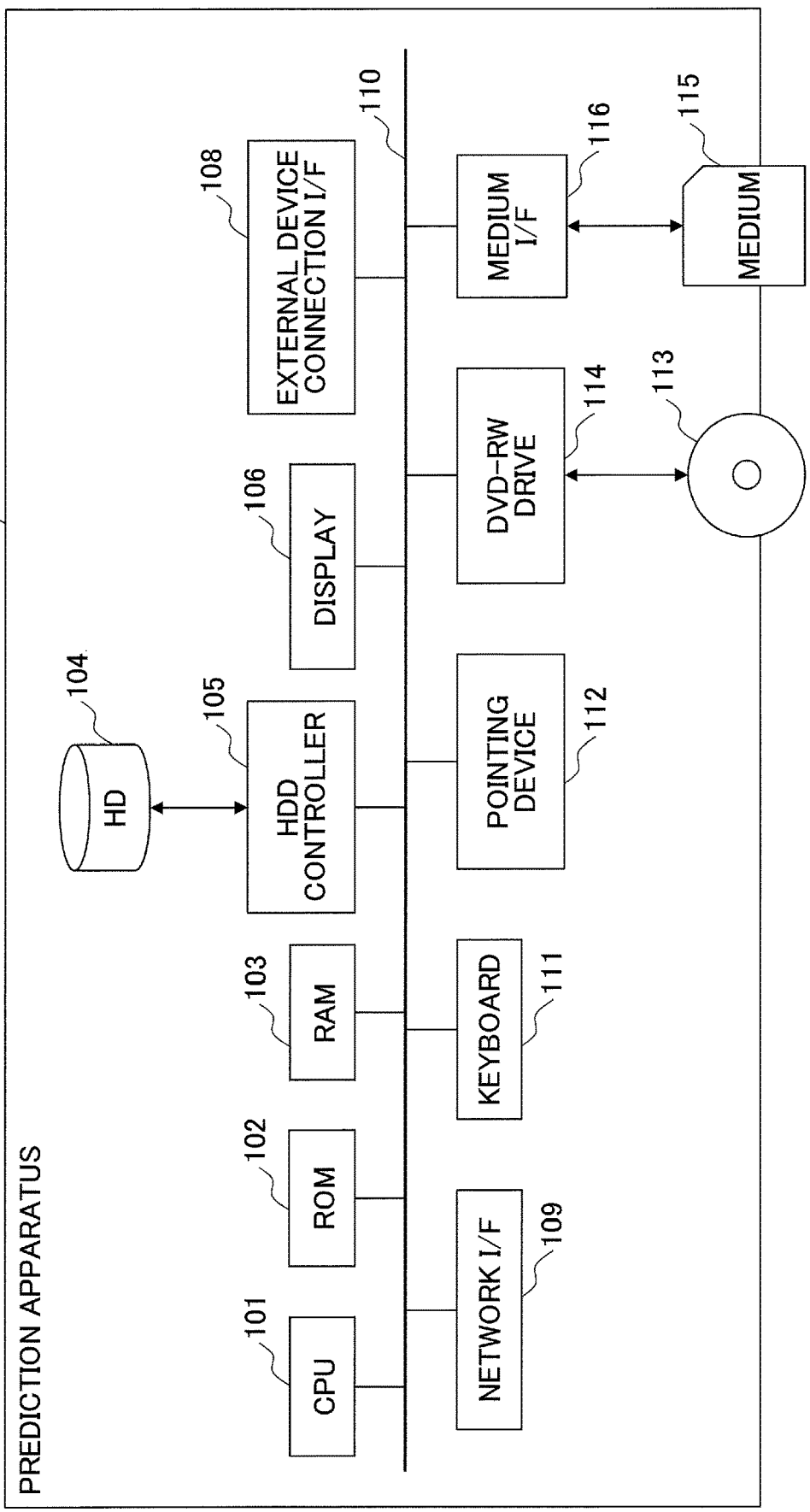
FIG. 2 is a hardware configuration diagram of a prediction apparatus according to an embodiment of the present invention.

FIG. 2 is a hardware configuration diagram of the prediction apparatus 10 according to an embodiment of the present invention.

FIG. 2 is a diagram illustrating the hardware configuration of the prediction apparatus 10. As illustrated in FIG. 2, the prediction apparatus 10 is constructed by a computer and includes a central processing unit (CPU) 101, a read-only memory (ROM) 102, a random access memory (RAM) 103, a hard disk (HD) 104, a hard disk drive (HDD) controller 105, a display 106, an external device connection I/F 108, a network I/F 109, a bus line 110, a keyboard 111, a pointing device 112, a Digital Versatile Disk Rewritable (DVD-RW) drive 114, and a medium I/F 116 as illustrated in FIG. 2.

Among these, the CPU 101 controls the operation of the entire prediction apparatus 10. The ROM 102 stores a program used to drive the CPU 101, such as an IPL. The RAM 103 is used as the work area of the CPU 101. The HD 104 stores various kinds of data such as programs. The HDD controller 105 controls the reading or writing of various kinds of data to the HD 104 in accordance with the control of the CPU 101. The display 106 displays various kinds of information such as cursors, menus, windows, characters, or images. The external device connection I/F 108 is an interface for connecting various external devices. In this case, the external device may be, for example, a USB memory or a printer. The network I/F 109 is an interface for performing data communication using a communication network. The bus line 110 is an address bus, data bus, or the like for electrically connecting components such as the CPU 101 illustrated in FIG. 2.

The keyboard 111 is a type of input unit including a plurality of keys for input of characters, numbers, various indications, and the like. The pointing device 112 is a type of input means for selecting and executing various instructions, selecting a processing target, moving a cursor, and the like. The DVD-RW drive 114 controls the reading or writing of various kinds of data to a DVD-RW 113 as an example of a removable recording medium. The recording medium is not limited to a DVD-RW, but may be a DVD recordable (DVD-R), etc. The medium I/F 116 controls the reading or writing (storage) of data to a recording medium 115, such as a flash memory.

<Functional Blocks>

FIG. 3 is a functional block diagram of the prediction apparatus 10 according to an embodiment of the present invention. As illustrated in FIG. 3, the prediction apparatus 10 may include a present position acquiring unit 201, a training dataset storage unit 202, a machine learning unit 203, a learned model storage unit 204, an inference unit 205, and a reporting unit 206. The prediction apparatus 10 can function as the present position acquiring unit 201, the machine learning unit 203, the inference unit 205, and the reporting unit 206 by executing a program. Each of the functions will be described below.

The present position acquiring unit 201 acquires a tag ID of the RFID tag 20 and an antenna ID of the RFID receiver 30 from the RFID receiver 30 via the Gateway 40. The present position acquiring unit 201 converts data of the acquired tag ID and antenna ID. Hereinafter, the conversion of data will be described with reference to FIG. FIGS. 4A and 4B.

FIGS. 4A and 4B are diagrams for describing pre-conversion data (data before conversion) and post-conversion data (data after conversion) according to an embodiment of the present invention. The pre-conversion data illustrated in FIG. 4 is the data acquired by the present position acquiring unit 201. As illustrated in FIG. 4A, the pre-conversion data includes the tag ID of the RFID tag 20, the antenna ID of the RFID receiver 30 that has read the RFID tag 20, and the date and time when the RFID receiver 30 has read the RFID tag 20. The post-conversion data in FIG. 4B is data after the present position acquiring unit 201 has converted the pre-conversion data of FIG. 4A. As illustrated in FIG. 4B, the post-conversion data includes information (e.g., name) for identifying the medical staff member 21 associated with the tag ID (i.e., the medical staff member 21 to which the RFID tag 20 is attached), information (e.g., a room number) for identifying the area associated with the antenna ID (i.e., the patient room in which the RFID receiver 30 is installed, etc.), and the date and time when the RFID receiver 30 has read the RFID tag 20.

Returning to FIG. 3, hereinafter, a <learning phase> and an <inference phase> will be described separately.
<Learning Phase>

The a training dataset storage unit 202 stores training dataset used for machine learning. The training dataset in the training dataset storage unit 202 is data converted into a predetermined format (that is, the post-conversion data of FIG. 4B) using the position information data acquired by the present position acquiring unit 201 for a certain period of time and accumulated therein. Hereinafter, the data stored in the training dataset storage unit 202 will be described with reference to FIG. 5.

FIG. 5 illustrates an example of data stored in the training dataset storage unit 202 according to an embodiment of the present invention. In the figure, "date time" represents the date and time of acquisition of the RFID tag 20 acquired by the present position acquiring unit 201. "Person" represents the medical staff member 21 (nurse A) wearing the RFID tag 20. A vector representing the area where the medical staff member 21 is located at each date and time (e.g., a vector representing a room number) is expressed as "101, 102, . . . 505". A training dataset including a plurality of pieces of the above-described time series data is stored in the training dataset storage unit 202.

Returning to FIG. 3, the machine learning unit 203 generates a learned model for deriving the position (i.e., the next position) of the movement destination of the RFID tag 20, from the position of the RFID tag 20 attached to the medical staff member 21. Specifically, the machine learning unit 203 performs machine learning using a training dataset, in which the area where the medical staff member 21 is located (e.g., a room number) is set as input data, and the area where the medical staff member 21 is located next (e.g., a room number) is set as output data, thereby generating a learned model. The machine learning unit 203 stores the generated learned model in the learned model storage unit 204.

The learned model storage unit 204 stores the learned model generated by the machine learning unit 203.
<<Present Time>>

In the <learning phase>, in addition to position information, information of the time at which the medical staff member 21 has been located at the corresponding position may also be learned. Specifically, the machine learning unit 203 performs machine learning using the training dataset in which the area where the medical staff member 21 is located (e.g., a room number) and the time at which the medical staff member 21 has been located in the corresponding area are set as input data, and the area where the medical staff member 21 is located next (e.g., a room number) is set as output data, thereby generating a learned model. In this case, it is possible to learn the movement according to the time period (for example, during daytime, the medical staff member 21 often moves from room 101 to room 102, but during nighttime, the medical staff member 21 often moves from room 101 to room 103, etc.).
<Inference Phase>

The inference unit 205 acquires the present position of the RFID tag 20 attached to the medical staff member 21 and infers the position of the movement destination (i.e., the next position) to which the RFID tag 20 will move.

Specifically, the inference unit 205 acquires, from the present position acquiring unit 201, information (e.g., name) for identifying the medical staff member 21 and information (e.g., room number) for identifying the area where the medical staff member 21 is located. Further, the inference unit 205 inputs the "area where the medical staff member 21 is located (e.g., the room number)" into the learned model in the learned model storage unit 204 and causes the learned model to output the "area where the medical staff member 21 will be located next (e.g., the room number)".

A model according to one embodiment of the present invention will now be described. In one embodiment of the invention, a model is constructed using Long Short-Term Memory (LSTM). Hereinafter, specific network configurations will be described with reference to FIG. 13, and specific parameters will be described with reference to FIG. 14.

Figure 13:
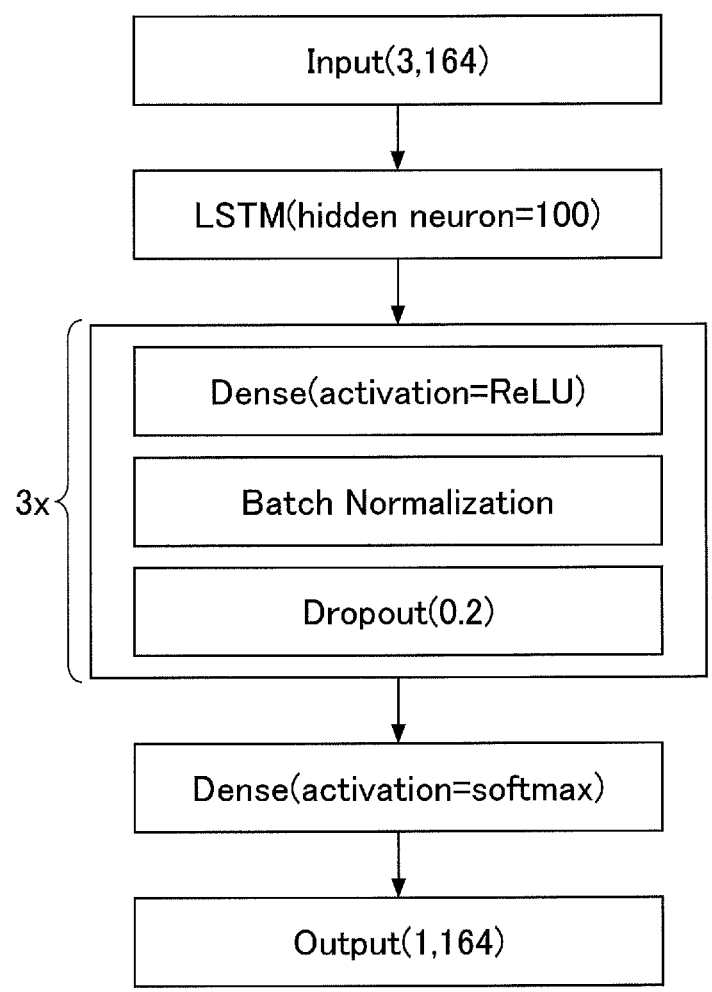
FIG. 13 illustrates a Long Short-Term Memory (LSTM) model structure according to an embodiment of the present invention.

FIG. 13 is a model structure of LSTM according to an embodiment of the present invention. As illustrated in FIG. 13, in the intermediate layer, a three-layer structure of a ReLU function, Batch Normalization, and Dropout=0.2 is applied to the activation function. Further, immediately before the output layer, a softmax function is used.

FIG. 14 indicates operation parameters in an LSTM model according to an embodiment of the present invention. As illustrated in FIG. 14, the "number of steps" is 3, 5, 10, the "mini batch size" is 128, and the "number of times of learning" is 25.
<<Present Time>>

In the <inference phase>, in addition to position information, information of the time at which the medical staff member 21 has been located at the present position may also be input to the learned model. Specifically, the inference unit 205 inputs "the area where the medical staff member 21 is located (e.g., the room number)" and "the date and time when the RFID receiver 30 has read the RFID tag 20" into the learned model in the learned model storage unit 204, and causes the learned model to output "the area where the medical staff member 21 will be located next (e.g., the room number)". In this case, it is possible to infer the movement according to the time period (for example, during daytime, the medical staff member 21 often moves from room 101 to room 102, but during nighttime, the medical staff member 21 often moves from room 101 to room 103, etc.).

Figure 6:
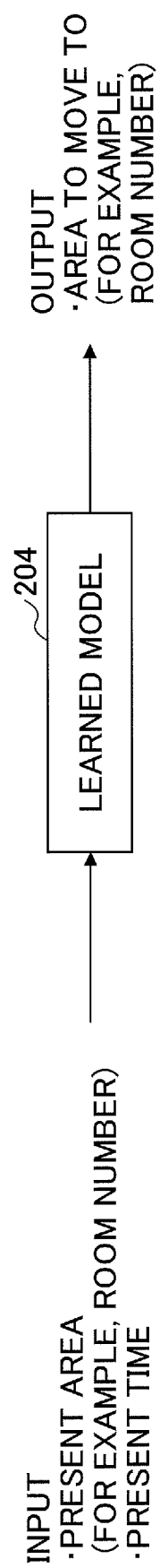
FIG. 6 is a diagram for explaining an inference phase according to an embodiment of the present invention.

FIG. 6 is a diagram for describing the inference phase according to an embodiment of the present invention. As illustrated in FIG. 6, when the learned model in the learned model storage unit 204 generated by the machine learning unit 203 accepts input of information of the present area (i.e., the present position of the RFID tag 20) where the medical staff member 21 is located (the present time may be added), the learned model outputs information of the area where the medical staff member 21 is to move to (i.e., the next position of the RFID tag 20).
<<Prediction of Flow Line>>

In the above <learning phase> and <inference phase>, a plurality of positions to move to next (i.e., a flow line) may be learned and inferred, rather than only the next immediate position to which the medical staff member moves. Specifically, the machine learning unit 203 performs machine learning by using a training dataset in which the area where the medical staff member 21 is located (e.g., a room number) is set as input data, and a plurality of areas where the medical staff member 21 is to move to next (i.e., the next area, the area after next, . . . ) are set as output data, thereby generating a learned model. The inference unit 205 inputs the "area where the medical staff member 21 is located (e.g., the room number)" into the learned model in the learned model storage unit 204, and causes the learned model to output a "plurality of areas where the medical staff member 21 is to move to (i.e., the next area, the area after next, . . . )."

<<Prediction of Position and Action>

In the above <learning phase> and <inference phase>, in addition to position information, information about the action of the medical staff member 21 may be learned and inferred. Specifically, the machine learning unit 203 performs machine learning using a training dataset, in which the area where the medical staff member 21 is located (e.g., a room number) is set as input data, and the area where the medical staff member 21 is located next (e.g., a room number) and the action in the next area are set as output data, thereby generating a learned model. The inference unit 205 inputs the "area where the medical staff member 21 is located (e.g., room number)" into the learned model in the learned model storage unit 204, and causes the learned model to output "an area (e.g., room number) where the medical staff member 21 will be located next (e.g., room number) and information about the action (action information) at the next position". For example, action information may include at least one of information of the action that the medical staff member 21 is to perform in an area such as a patient room, and information of what is needed to perform the action. In this case, the training dataset may be generated based on a diary and the like of the medical staff member 21.

Any combination of the above-described <<present time>>, <<prediction of flow line>>, and <<prediction of position and action>> is possible.

Here, the data format of the input data and output data according to one embodiment of the present invention will be described. Referring to FIGS. 15A and 15B, the case of inferring the area to which the medical staff member 21 is to move (i.e., the next position of the RFID tag 20) will be described, and referring to FIGS. 16A and 16B, the case of inferring the area to which the medical staff member 21 is to move (i.e., the next position of the RFID tag 20) and the information of the action at the next position, will be described.

FIGS. 15A and 15B illustrate data formats of input data and output data according to an embodiment of the present invention.

The input data includes the date and time ("date time" in FIG. 15A) and the area where the medical staff member 21 is located at the corresponding date and time ("101, 102, . . . , 505" in FIG. 15A). In the example of FIG. 15A, room 102 at 12:10 on Nov. 1, 2019, room 101 at 12:15 on Nov. 1, 2019, and room 102 at 12:20 on Nov. 1, 2019 are used as input data.

The output data includes the date and time (the "date time" in FIG. 15B) and the area where the medical staff member 21 is to move to at the date and time (the "101, 102, . . . , 505" in FIG. 15B; note that the area with the highest probability is set as the next movement destination). In the example of FIG. 15B, it is inferred, from the above input data, that the medical staff member 21 is to move to room 101 at 12:25 on Nov. 1, 2019.

Note that when predicting a plurality of movement destinations (that is, when predicting a flow line), the prediction is performed again using, as input data, the prediction result (output data of FIG. 15B) and a predetermined number of pieces of data from the most recent data among the input data (data at 12:15 and data at 12:20 in the example of FIG. 15A).

Figure 12:
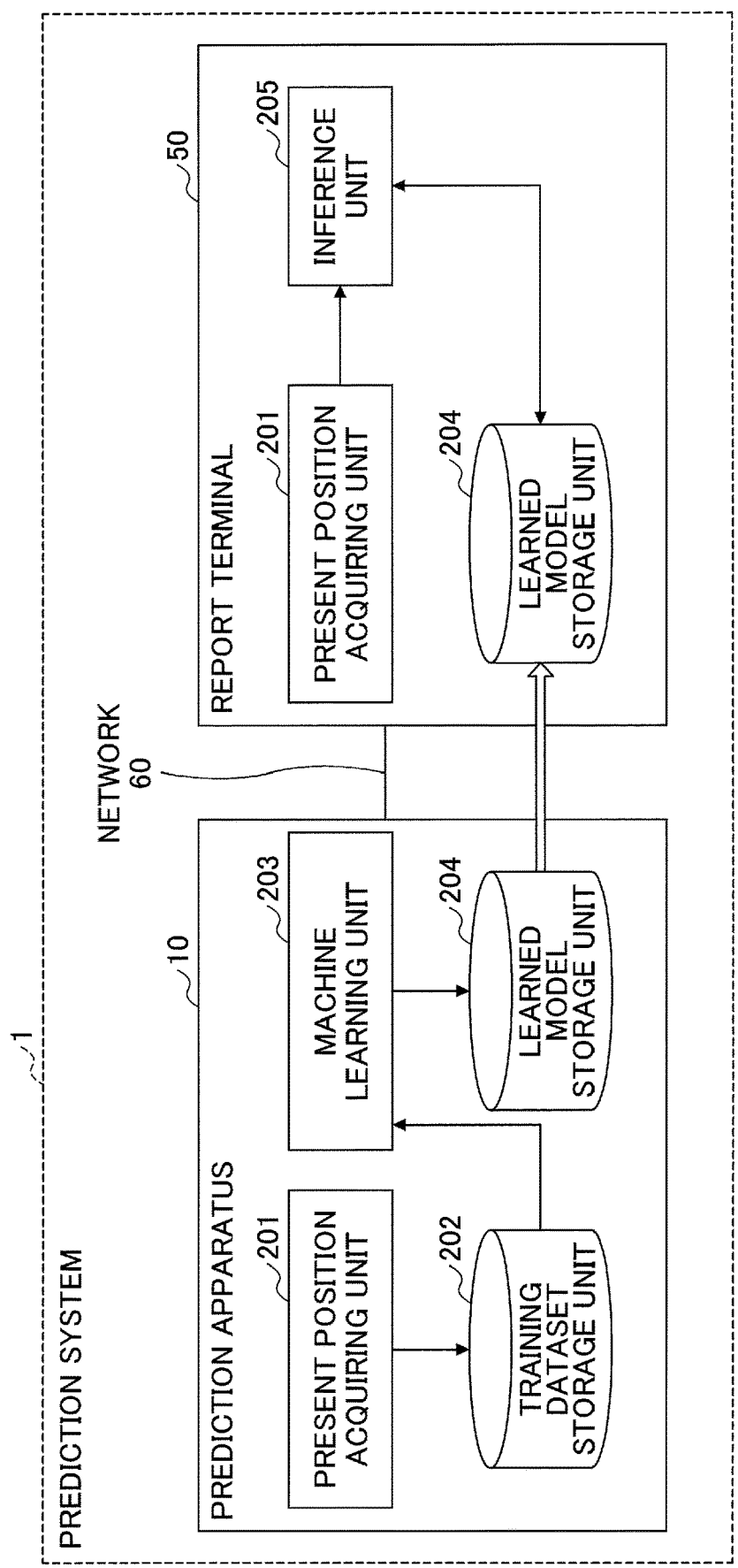
FIG. 12 is a configuration diagram of the entire prediction system according to an embodiment of the present invention.

FIGS. 16A and 16B illustrate data formats of input data and output data according to an embodiment of the present invention The input data includes the date and time (date time in FIG. 16A), the medical staff member 21 (person in FIG. 16A), and the area where the medical staff member 21 is located at the corresponding date and time ("101, 102, . . . , 505" in FIG. 16A). In the example of FIG. 16A, 12:10 on Nov. 1, 2019 and nurse A and room 102; 12:15 on Nov. 1, 2019 and nurse A and room 101; and 12:20 on Nov. 1, 2019 and nurse A and room 102, are used as the input data.

The output data includes the date and time (date time in FIG. 16B), the medical staff member 21 (person in FIG. 16B), and the area where the medical staff member 21 is to move to at the date and time (the "101, 102, . . . , 505" in FIG. 16B; note that the area with the highest probability is set as the next movement destination), and information about the action at the next location (action in FIG. 16B). In the example of FIG. 16B, it is inferred, from the above input data, that the medical staff member 21 (nurse A) is to move to room 101 at 12:25 on Nov. 1, 2019 to perform an action related to a medical examination.

Note that when predicting a plurality of movement destinations (that is, predicting a flow line), the same method as that illustrated in FIGS. 15A and 15B is used.

The reporting unit 206 reports, to the report terminal 50, the result inferred by the inference unit 205 (that is, the area (e.g., room number) to which the medical staff member 21 is to move). As described above, the reporting unit 206 may send a report such that the report terminal 50 displays the report on a screen or may send a report such that the report terminal 50 outputs the report by voice sound. In addition to reporting the next position, the reporting unit 206 may be configured to report the information about the action to be performed at the next position.

Hereinafter, functions that can be added to the above-described embodiments will be described.

<<Aberration Detection>>

In one embodiment of the present invention, the prediction apparatus 10 may further include an aberration detecting unit that deletes data, in which an aberration is detected, from the data acquired by the present position acquiring unit 201 during a certain period of time in the past, and then sets the resulting data as the training dataset. Hereinafter, the aberration detection will be described with reference to FIG. 7.

Figure 7:
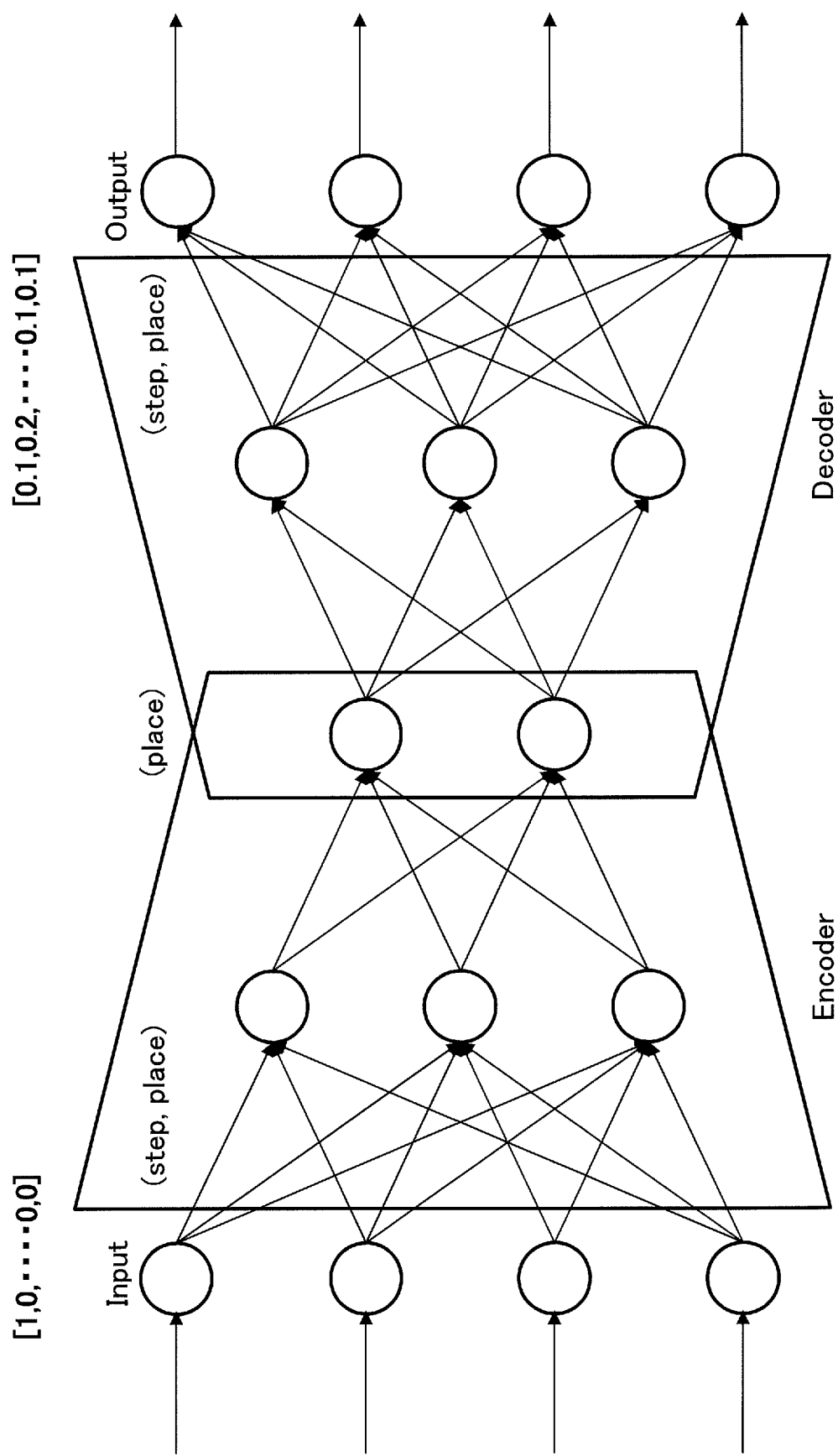
FIG. 7 is a diagram for explaining aberration detection according to an embodiment of the present invention.

FIG. 7 is an example of a neural network for detecting aberrations according to an embodiment of the present invention. The neural network is used in the data processing that is the pre-process of generating the training dataset to be stored in the training dataset storage unit 202 of FIG. 3. The neural network includes an encoder unit which outputs the next position as a prediction result when a movement history (position information history) of the medical staff member 21 of a certain period of time in the past is input, and a decoder unit which outputs a movement history in the past from the output next position.

When the difference between the input vector input to the encoder unit (a vector representing the area where the medical staff member 21 is located, such as a room number) and the output vector output from the decoder unit, is greater than or equal to a predetermined reference, the corresponding data is deleted from the candidate of a training dataset.

In this way, among the information of the position of the RFID tag 20 attached to the medical staff member 21, data relating to the information of a position determined to be aberrant (e.g., information of an irregular movement of the medical staff member 21) is deleted from the candidate of a training dataset. Then, the cleansed data is used for predicting the movement and the action, and, therefore, it is possible to improve the accuracy of the training dataset.

<<Clustering>>

In one embodiment of the present invention, the medical staff members 21 may be clustered based on movement patterns so as to predict the movement destination and the action of the medical staff member 21 for each cluster (i.e., to generate a learned model for each cluster). Specifically, a learned model according to the attributes common to the medical staff members 21 belonging to the cluster is used. Accordingly, it is possible to improve the accuracy in the prediction of the movement and the action of the medical staff member 21.

<<Matching with Various Schedules>>

In one embodiment of the present invention, the predicted movement destination and action may be matched with the schedule of the medical facility or the medical staff member 21 to eliminate inappropriate prediction results (e.g., unrealistic prediction results in view of the schedule of the medical facility or the medical staff member 21).

<Processing Method>

A method of the learning process and the inference process will be described below.

Figure 8:
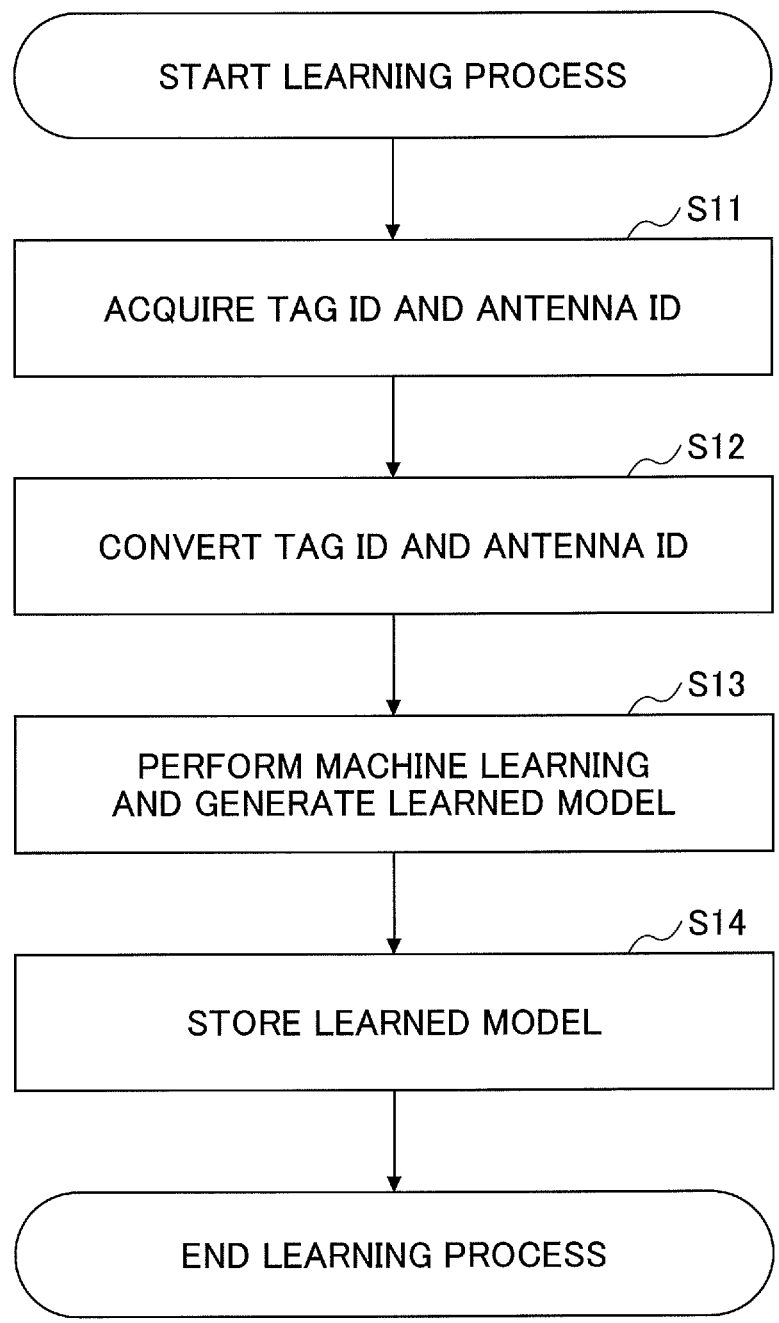
FIG. 8 is a flowchart of a learning process according to an embodiment of the present invention.

FIG. 8 is a flowchart of a learning process according to an embodiment of the present invention.

In step S11, the present position acquiring unit 201 acquires the tag ID of the RFID tag 20 and the antenna ID of the RFID receiver 30 that has read the RFID tag 20.

In step S12, the present position acquiring unit 201 converts the tag ID and the antenna ID acquired in step S11 into information (e.g., name) for identifying the medical staff member 21 associated with the tag ID and information (e.g., room number) for identifying the area associated with the antenna ID, respectively.

In step S13, the machine learning unit 203 performs machine learning using the post-conversion data of step S12 (that is, time series data of the vector representing the area where the medical staff member 21 is located (for example, a vector representing the room number)) as the training dataset. Specifically, the machine learning unit 203 performs machine learning using the training dataset in which the area where the medical staff member 21 is located (e.g., the room number) is set as the input data and the area where the medical staff member 21 is to be located next (e.g., the room number) is set as the output data, thereby generating a learned model.

In step S14, the machine learning unit 203 stores the learned model generated in S13 in the learned model storage unit 204.

Figure 9:
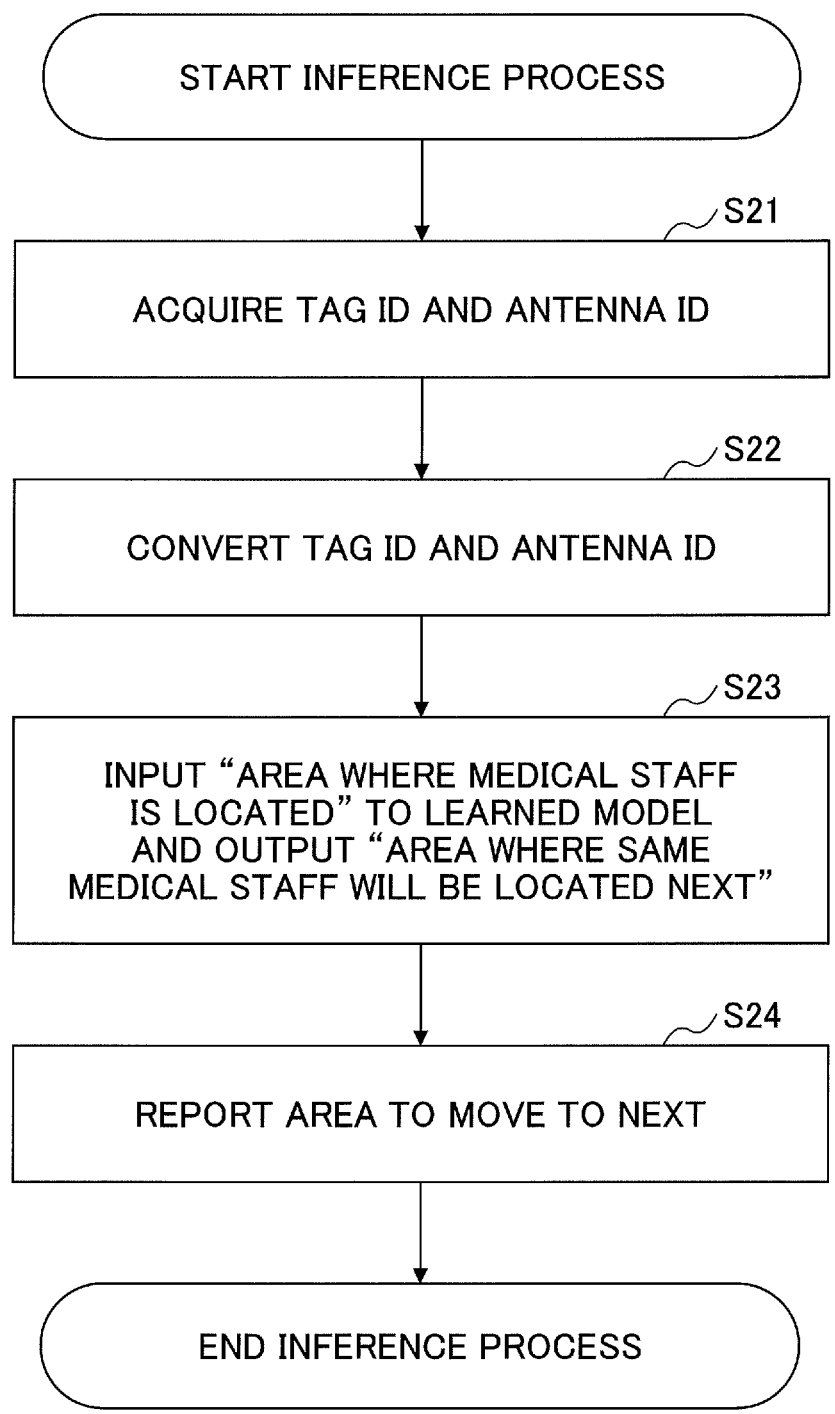
FIG. 9 is a flowchart of an inference process according to an embodiment of the present invention.

FIG. 9 is a flowchart of an inference process according to one embodiment of the present invention.

In step S21, the present position acquiring unit 201 acquires the tag ID of the RFID tag 20 and the antenna ID of the RFID receiver 30 that has read the RFID tag 20.

In step S22, the present position acquiring unit 201 converts the tag ID and the antenna ID acquired in S21 to information (e.g., name) for identifying the medical staff member 21 associated with the tag ID and information (e.g., room number) for identifying the area associated with the antenna ID, respectively.

In step S23, the inference unit 205 inputs the "area (e.g., room number) where the medical staff member 21 is located" of step S22 to the learned model in the learned model storage unit 204, and causes the learned model to output the "area (e.g., room number) where the medical staff member 21 will be located next".

In step S24, the reporting unit 206 reports, to the report terminal 50, the result inferred by the inference unit 205 in step S23.

Figure 10:
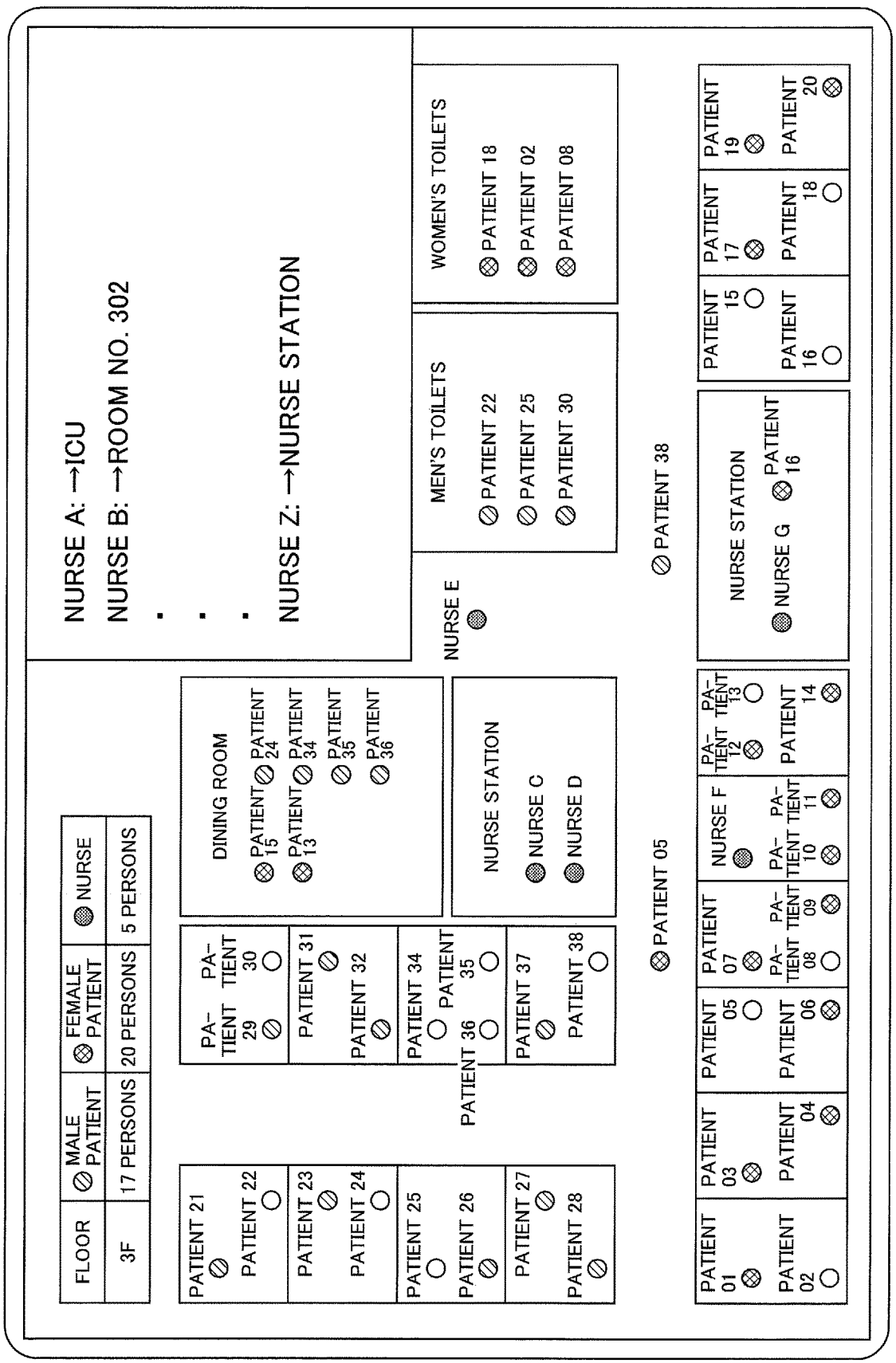
FIG. 10 illustrates an example of a screen displayed on a report terminal according to an embodiment of the present invention.
Figure 11:
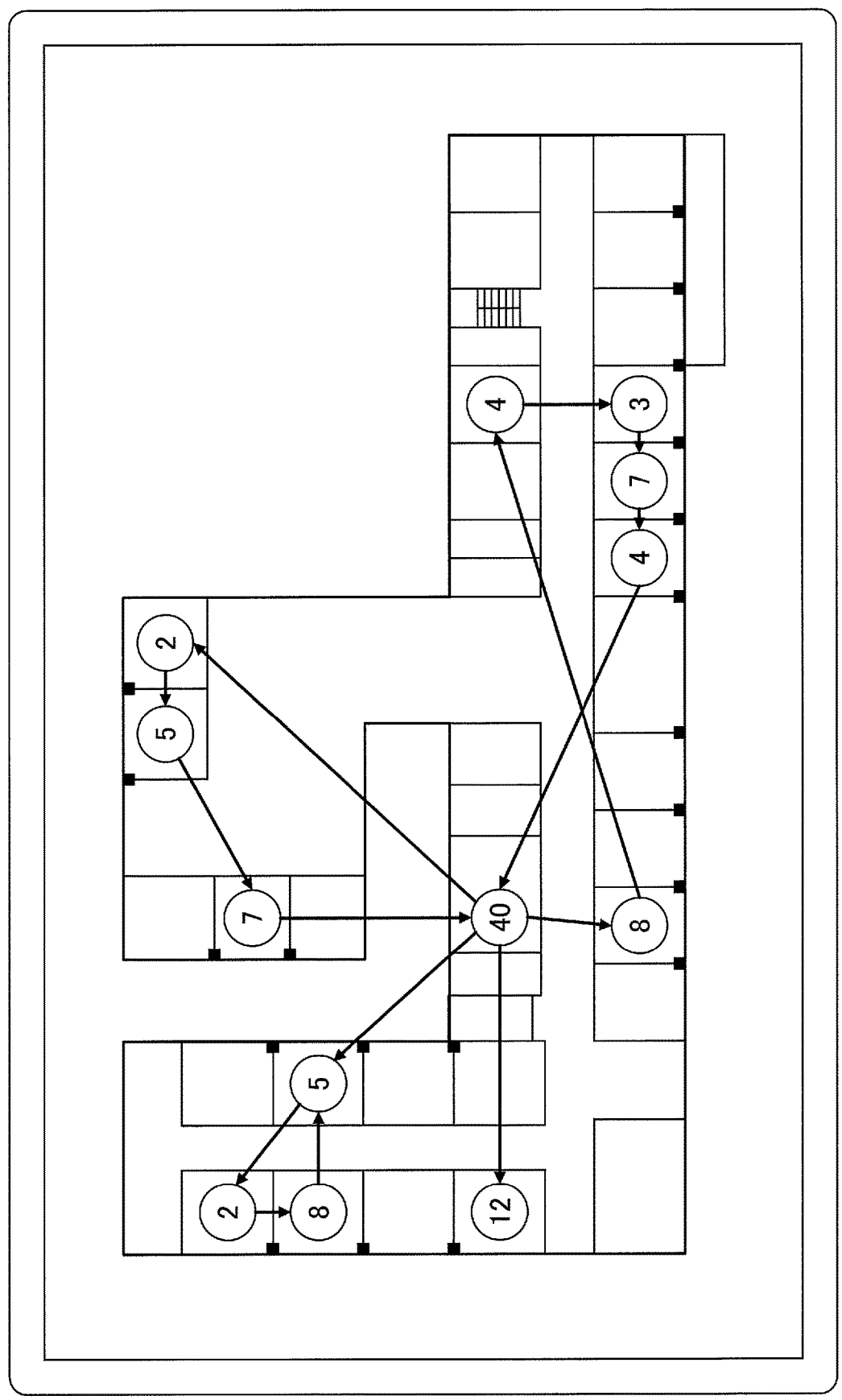
FIG. 11 illustrates an example of a screen displayed on the report terminal according to an embodiment of the present invention.

FIGS. 10 and 11 are examples of a screen displayed on the report terminal 50 according to an embodiment of the present invention. For example, as illustrated in FIG. 10, the next immediate position (e.g., patient room, treatment room, nurse station, etc.) to which each of the one or more medical staff members 21 moves, may displayed on the screen of the report terminal 50. Alternatively, for example, as illustrated in FIG. 11, a flow line indicating a plurality of positions (e.g., patient room, treatment room, nurse station, etc.) to which one or more medical staff members 21 are to move next, may displayed on the screen of the report terminal 50.

Other Embodiments

In an embodiment of the present invention, the report terminal 50 or a computer connected to the report terminal 50 (e.g., a computer installed in a hospital) may include some or all of the functions of the prediction apparatus 10. For example, in the example of FIG. 12, the prediction apparatus 10 includes the machine learning unit 203 and the report terminal 50 includes the inference unit 205. The machine learning unit 203 of the prediction apparatus 10 performs the above-described <learning phase>, and the inference unit 205 of the report terminal 50 performs the above-described <inference phase>. Specifically, the prediction apparatus 10 performs a process of machine learning to generate a learned model. The report terminal 50 performs a process of inference using the learned model generated by the prediction apparatus 10.

<Application to Other Fields>

While the embodiments have been described in the context of a medical setting relating to medical staff members, the prediction system, apparatus, method, and program of the present invention may be utilized for applications other than medical staff members in the medical setting. For example, it is possible to predict the movement and action of patients in medical facilities such as hospitals and residents in nursing homes, and to predict the movement and action of employees in plant production lines, and to predict the movement and action of tourists.

Thus, in one embodiment of the present invention, the movement destination (i.e., the next position) can be predicted based on the present position of the medical staff member or the like. In the prediction, movements of medical staff members, etc., according to time periods, can be taken into account. Therefore, it is possible to predict the movement destination depending on the hospital situation and the medical staff member's work schedule.

The functions of each of the embodiments described above may be implemented by one or more processing circuits. As used herein, a "processing circuit" includes a processor programmed to execute each function by software such as a processor implemented in an electronic circuit; or devices such as an Application Specific Integrated Circuit (ASIC) a digital signal processor (DSP), a field programmable gate array (FPGA), and a conventional circuit module, designed to execute each function as described above.

According to one embodiment of the present invention, it is possible to predict the movement destination of a person, such as a medical staff member, to which a wireless device is attached.

The information processing apparatus, the method, and the information processing system are not limited to the specific embodiments described in the detailed description, and variations and modifications may be made without departing from the spirit and scope of the present invention.

What is claimed is:

1. An information processing apparatus comprising a processor, in communication with a memory, executing a process including:
    acquiring identification information of a wireless device and information for identifying a position of the wireless device;
    storing a learned model generated by performing machine learning by using a training dataset including a position of a person to which the wireless device is attached and a movement destination of the person to which the wireless device is attached;
    inferring the movement destination of the person to which the wireless device is attached from the position of the wireless device, based on the learned model; and
    reporting the inferred movement destination, wherein
        the learned model is generated by performing the machine learning by using the training dataset including the position of the person to which the wireless device is attached, the movement destination of the person to which the wireless device is attached, and information of an action performed at the movement destination, and
        the inferring includes inferring the movement destination of the person to which the wireless device is attached and the information of the action performed at the movement destination, based on the position of the wireless device.

2. The information processing apparatus according to claim 1, wherein
    the training dataset includes a time at which the identification information of the wireless device and the information for identifying the position of the wireless device have been acquired, and
    the inferring is based on the time at which the identification information of the wireless device and the information for identifying the position of the wireless device have been acquired.

3. The information processing apparatus according to claim 1, wherein the training dataset is obtained by deleting aberrant data, which is detected as including an aberration, from the acquired information for identifying the position of the wireless device.

4. The information processing apparatus according to claim 3, wherein the process further includes:
    deleting, from a candidate of the training dataset, an input value of past position information of the person to which the wireless device is attached and an output value obtained by performing a predetermined calculation process on the input value, upon determining that the input value and the output value are aberrant values upon detecting that a difference between a tendency of the input value and a tendency of the output value exceeds a predetermined reference.

5. The information processing apparatus according to claim 1, wherein the reporting includes causing the movement destination of the person to which the wireless device is attached to be displayed on a screen of a report terminal or causing the movement destination of the person to which the wireless device is attached to be output by voice sound from the report terminal.

6. The information processing apparatus according to claim 1, wherein the reporting includes reporting one of the movement destinations of the person to which the wireless device is attached or reporting a flow line indicating a plurality of the movement destinations of the person to which the wireless device is attached.

7. An information processing system comprising:
    a wireless device; and
    a processor, in communication with a memory, executing a process including:
        acquiring identification information of the wireless device and information for identifying a position of the wireless device;
        storing a learned model generated by performing machine learning by using a training dataset including a position of a person to which the wireless device is attached and a movement destination of the person to which the wireless device is attached;
        inferring the movement destination of the person to which the wireless device is attached from the position of the wireless device, based on the learned model; and
    reporting the inferred movement destination, wherein
        the learned model is generated by performing the machine learning by using the training dataset including the position of the person to which the wireless device is attached, the movement destination of the person to which the wireless device is attached, and information of an action performed at the movement destination,
        the inferring includes inferring the movement destination of the person to which the wireless device is attached and the information of the action performed at the movement destination, based on the position of the wireless device, and
        the wireless device is a radio frequency identifier tag.

8. A method executed by a computer, the method comprising:
    acquiring identification information of a wireless device and information for identifying a position of the wireless device;
    inferring a movement destination of a person to which the wireless device is attached from the position of the wireless device, based on a learned model generated by performing machine learning by using a training dataset including a position of the person to which the wireless device is attached and the movement destination of the person to which the wireless device is attached; and
    reporting the inferred movement destination, wherein
        the learned model is generated by performing the machine learning by using the training dataset including the position of the person to which the wireless device is attached, the movement destination of the person to which the wireless device is attached, and information of an action performed at the movement destination, and
        the inferring includes inferring the movement destination of the person to which the wireless device is attached and the information of the action performed at the movement destination, based on the position of the wireless device.

* * * * *